US006683680B2

(12) United States Patent
Dinu et al.

(10) Patent No.: US 6,683,680 B2
(45) Date of Patent: Jan. 27, 2004

(54) METHOD, SYSTEM AND DEVICE PROVIDING A MUSICAL REPRESENTATION OF A TRANSPARENT OR TRANSLUCENT STRUCTURE

(75) Inventors: Nicolae Dinu, Mississauga (CA); Gideon Tolkowsky, Herzlya (IL); Gabi Tolkowsky, Antwerpen (BE); Uri Tolkowsky, Natanya (IL)

(73) Assignee: Crystal Beam Melody, Inc., Wilmington, DE (US)

( * ) Notice: Subject to any disclaimer, the term of this patent is extended or adjusted under 35 U.S.C. 154(b) by 281 days.

(21) Appl. No.: 09/739,713

(22) Filed: Dec. 20, 2000

(65) Prior Publication Data

US 2001/0006415 A1 Jul. 5, 2001

(51) Int. Cl.[7] ............................................... G01N 21/87
(52) U.S. Cl. .......................................... 356/30; 356/71
(58) Field of Search .................................... 356/30, 71

(56) References Cited

U.S. PATENT DOCUMENTS

| | | | | | |
|---|---|---|---|---|---|
| 4,364,472 A | * | 12/1982 | Waldmeier | ............... | 206/459.5 |
| 4,563,771 A | * | 1/1986 | Gorgone et al. | ............. | 382/135 |
| 4,882,966 A | * | 11/1989 | Silverman | .................... | 84/94.2 |
| 5,097,376 A | * | 3/1992 | Khan | .......................... | 242/341 |
| 5,245,875 A | | 9/1993 | Tyrode | | |
| 5,828,405 A | | 10/1998 | Vanier et al. | | |
| 5,954,194 A | * | 9/1999 | Simpson | ....................... | 206/96 |
| 6,110,124 A | * | 8/2000 | Cheng | ......................... | 600/549 |
| 6,405,858 B1 | * | 6/2002 | Gagliardi | ..................... | 206/6.1 |

FOREIGN PATENT DOCUMENTS

| | | | |
|---|---|---|---|
| EP | 0235460 | * | 9/1987 |
| JP | 56-137235 | * | 10/1981 |
| WO | WO 93/12496 | | 6/1993 |

* cited by examiner

Primary Examiner—F. L. Evans

(57) ABSTRACT

A method and system are provided for representing a structure of a kind characterized by a specific radiation response to a predetermined incident radiation. The incident radiation is applied to the structure to produce the radiation response thereof, which is detected and data indicative thereof is generated. This data is processed and analyzed to produce a predetermined output representative of a structure-related data. The output includes a non-visual portion derived from the specific radiation response of the structure and is sensory perceptible by a human being.

34 Claims, 5 Drawing Sheets

METHOD, SYSTEM AND DEVICE PROVIDING A MUSICAL REPRESENTATION OF A TRANSPARENT OR TRANSLUCENT STRUCTURE

FIELD OF THE INVENTION

The present invention relates to a method and system for representing a structure of the kind characterized by a specific signature, as well as a device for the structure presentation. The invention is particularly useful for representing such structures as gemstones according to their specific radiation response for marketing purposes.

BACKGROUND OF THE INVENTION

It is known to use images (e.g., photos) of various items for marketing purposes. Commercial items are typically advertised in printed catalogs or over the Internet. However, for such complicated and expensive structures as gemstones, or structures having sentimental meaning, producing an image of the structure is not adequate for authenticating a gemstone structure (distinguishing it from other similar structures).

There are a number of arrangements for using optical techniques to obtain an optical signature of a gemstone. It has been found that the reflection and refraction characteristics of a gemstone, in particular, a diamond, define a unique pattern for that particular gemstone, which can be used to identify the gemstone. This technique can also be used for synthetic stones, crystal and other structures. Systems for classifying and identifying gemstones are disclosed for example in U.S. Pat. Nos. 5,124,935 and 5,828,405.

Gemprint Corporation markets a system and manages a database where the optical responses of gemstones are determined and the optical responses are recorded in a database for future reference. The optical response of gemstones has been determined by courts to be sufficiently unique to distinguish one gemstone from another.

The optical response of a gemstone is influenced by the position that the gemstone is secured in within the device and any misalignment of the axis of the gemstone distorts the optical response. It may also be necessary to rotate and correct the image for distribution to compare one optical response for a gemstone with a previously recorded optical response of the gemstone.

The system commercially available from the Gemprint Corporation allows the comparison of a first optical response with a second optical response and allows both of these responses to be displayed on a computer monitor and appropriately rotated and overlayed. The computer system provides a comparison of the two optical records. The final determination of a match is often confirmed by a skilled person comparing the two optical responses.

The purchaser of a diamond and the determination of the value of a diamond is a function of its size and weight, the cut of the stone, the clarity of the stone, and other features. However, many of these technical features and physical characteristics are difficult to appreciate by the purchaser.

SUMMARY OF THE INVENTION

There is a need in the art to facilitate the representation of a structure having a specific signature, by providing a novel method and system for the structure representation, as well as the structure presentation device, and a method for selling such structures. Additionally, the present invention enables verification of the structure signature to ensure the authenticity of the structure.

The term "specific signature of a structure" used herein signifies a specific radiation response of the structure (e.g., gemstone) to predetermined incident radiation (e.g., defined by the reflection and refraction characteristics of a gemstone). Such a structure may be a crystal (e.g., a fine crystal object), gemstone, logo, symbol, etc., made out of any material. It should be understood that the term "specific" relates to a specific structure (i.e., unique structure such as a diamond), or a structure of a specific kind (i.e., structures that are reproducible, e.g., fine crystal objects, and therefore are characterized by the similar radiation response).

It should also be noted that, in the example of gemstones, the specific signature of the gemstone may and may not be that of the gemstone intended for sale. It is often the case that the gemstone to be sold is a cut and polished gemstone. The specific signature of the gemstone to be sold, however, may be that measured on its rough state, i.e., prior to being cut and polished.

The present invention uses the specific structure signature to produce an output, which is based upon a bitmap corresponding to this specific signature, and includes a non-visual portion derived from the specific radiation response which is sensory perceptible by a human being. Such a non-visual portion of the output may be music (e.g., song), any other audio message, or perfume corresponding to the specific radiation response of a structure obtained by translating a bitmap of the radiation response.

In other words, the output is indicative of at least non-visual, sensory perceptible equivalent of the structure signature. Additionally, the output, which is sensory perceptible by a human being, may also include at least one of the following: specific data related to (selected by) a structure-receiver, a structure-manufacturer, and a structure-vendor.

Generally speaking, the main idea of the present invention consists of providing the entire structure-related data (i.e., data representative of a structure) by determining the specific structure signature (radiation response), and producing an output including a sensory perceptible, non-visual equivalent of the structure signature. Preferably, the output also includes additional information assigned to the specific structure which is selected by a structure-receiver, structure manufacturer and/or structure-vendor.

Thus, the term "structure-related data" used herein signifies data including at least data representative of the structure signature based upon a bitmap thereof, and, optionally, also data representative of at least one of the following: a structure-receiver, structure-manufacturer and structure-vendor.

A gemstone-structure may be a part of a jewelry piece. In this specific example, it should be understood that the term "structure-related data" may signify data representative of the radiation response of at least one of the following: one-gemstone structure, multiple-gemstone structure, and a jewelry piece including one or more gemstone-structures.

The term "structure-receiver" used herein signifies a person purchasing the structure, a person for whom the structure is purchased, or both, as well as the structure-vendor, who also may present a structure-receiver, when purchasing the structure from its manufacturer (or another authorized person on his behalf), and may further sell the structure to another party, i.e., a further structure-receiver. The structure-receiver-related data is selected in accordance with his preferences (priorities). This may, for example, be associated with one or more messages to be presented to the structure-receiver together with the structure (e.g., as a gift). This message may relate to the receiver's birthday and be identified, for example, by corresponding astrological data (e.g., data concerning the position of stars at the receiver's home-place and on his birthday).

The gemstone's signature may be indicative of data (e.g., identification code) engraved or presented by any suitable means on the gemstone's girdle, table ('Diamond: Natural, Treated or Synthetic?—Identification at the start of the new millenium', Van Royen J., Van Esbroeck V, Antwerp Facets—Publication of the Diamond High Council, No. 32, September 1999, p. 15), or any other location of the gemstone or a jewelry piece containing the same. The gemstone- or the like structure-related data may include, in addition to data representative of its radiation response, data representative of another character of the structure, such as its weight and/or moment of inertia and/or resonance condition.

There is thus provided, according to one aspect of the present invention, a method for representing a structure of a kind characterized by a specific radiation response to a predetermined incident radiation, the method comprising the steps of:

(a) applying the incident radiation to the structure to produce the radiation response thereof;

(b) detecting said radiation response and generating data indicative thereof;

(c) processing and analyzing the generated data to produce an output representative of a structure-related data, wherein said output includes a non-visual portion derived from the specific radiation response which is sensory perceptible by a human being.

Preferably, the incident radiation is optical, but may be other electromagnetic or acoustic radiation.

In order to make the output sensory perceptible by a human being, it may include music (e.g., song, melody) and/or acoustic message, and may also include a perfume. To this end, the processing of the data indicative of the radiation response (e.g., bitmap) utilizes a suitable data translation technique. If a perfume is to be included, for example a known Digital Aroma Generation technique developed by an American Company and disclosed in the Internet Site Aromajet.com., can be used. The output may be formatted for presentation through a communication network, such as the Internet to be presented on an Internet Site.

Needless to say that in the case of music or sound representing a structure, the present invention provides for visually impaired or blind people to enjoy such a wonderful purchase or gift.

As indicated above, the output may include additional data selected by structure-manufacture and/or structure-vendor and/or structure-receiver. This additional portion of the output may include visual signals, e.g., of a kind to be displayed on a monitor (of a computer, TV set, or any other type of electro-optical display). Such a visual signal may be a picture (e.g., an astrological map), photo, message. It should be noted that the output may be specifically encoded to cause generation (e.g., periodical) of desired output signals, for example, the output, when being readable by a computer device, may cause periodical presentation of one or more selected messages to a structure-receiver during a certain time interval. The structure-receiver may himself define the appearance of such output signals.

According to another aspect of the present invention, there is provided a system for representing a structure of a kind characterized by a specific radiation response to a predetermined incident radiation, the system comprising:

(One) a radiation source generating the incident radiation to be applied to said structure to produce the specific radiation response thereof;

(Two) a detector means for detecting the radiation response and generating data indicative thereof;

(Three) a data processing and analyzing utility for processing the generated data to produce an output representative of a structure-related data, wherein said output includes a non-visual portion derived from said specific radiation response of the structure and being sensory perceptible by a human being; and (Four) a data presentation utility for presenting said output.

Preferably, the system also comprises a database representative of various kinds of information to be selected by an authorized person (e.g., structure-receiver) and to be included in the output. The database may be accommodated remotely from the above elements of the system and be accessible through a communication network, e.g., the Internet. If the information to be selected includes perfumes, the system also comprises a unit containing specific scent compounds to be activated by software (of the data processing and analyzing utility) in accordance with the selected corresponding digital information (from the database).

According to yet another aspect of the invention, there is provided a device for presentation of a structure, which is characterized by a specific radiation response to a predetermined incident radiation, the device comprising a data representing utility operable to generate a signal, which enables presentation of a predetermined output representative of structure-related data, wherein said predetermined output includes a non-visual portion derived from the specific radiation response and being sensory perceptible by a human being.

It should be understood that the data representing utility may and may not include an output utility for presenting said predetermined output, but is of a kind enabling (causing) the presentation of this output. More specifically, the signal generated by the data representing utility provides access to the predetermined output representative of the structure-related data. This predetermined output may be stored in a memory of the data representing utility, or in that of an external system (computer, phone, TV, etc.). If an external system is considered, the signal generated by the data representing utility is of a kind allowing communication with the external system (through wires or wireless).

There is also provided according to the present invention, a method of selling a structure characterized by a specific structure signature in the form of a specific radiation response of the structure to a predetermined incident radiation, the method comprising the step of providing a data representing utility operable to generate a signal, which enables presentation of a predetermined output representative of structure-related data, wherein said predetermined output includes a non-visual portion derived from said specific radiation response and being sensory perceptible by a human being, said data representing utility being supplied with the structure to be sold.

A purchased structure (which may be a gemstone that may be included in a jewelry piece) is typically supplied in a box, which, according to the present invention, serves as a structure presentation case. The presentation case is equipped with a data representing utility of a kind enabling presentation of the output representative of the structure-related data, and possibly, also a means for enabling verification of the structure signature, thereby allowing for authentication of the structure contained in the case.

Thus, according to yet another aspect of the present invention, there is provided a device for presentation of a structure, which is characterized by a specific structure signature in the form of a specific radiation response to a predetermined incident radiation, the device comprising:

a presentation case for containing the structure therein; and a data representing utility operable to generate a signal, which enables presentation of a predetermined output representative of structure-related data, wherein said predetermined output includes a non-visual portion derived from said specific structure signature and being sensory perceptible by a human being.

The data representing utility may include only a readable medium (e.g., disc), which carries previously recorded data representative of the structure, and is of a kind readable by an external data retrieval unit (e.g., computer). The data representing utility may include an electronic assembly incorporating both a memory storing the previously recorded data representative of the structure, and a data retrieval utility generating the signal that enables the presentation of the predetermined output. The recorded data representative of the structure may comprise the entire structure-related data (i.e., the predetermined output) to be presented to the structure-receiver together with the structure. The recorded data representative of the structure may comprise only a part (fragment) of the entire structure-related data, which serves as a key code for accessing the entire structure-related data at an external device, e.g., through the Internet. Such a fragment of the structure-related data may be a part of a bitmap representative of the specific radiation response of the structure, and/or weight, and/or moment of inertia. The data representing utility may comprise also an output, data-presentation utility (e.g., display and/or speaker device) for presenting said predetermined output sensory perceptible by a human being.

The data representing utility may comprise a structure signature verification assembly, which comprises a measuring unit of a kind capable of determining a character of the structure (e.g., physical parameter or any reference mark incorporated in or attached to the structure) and generating data indicative thereof, and a data processing and analyzing utility. The measuring unit may include an optical system (composed of a radiation source and a detector) for determining the radiation response of the structure and/or an identification code assigned to the structure and incorporated in or attached to the structure. The measuring unit may be of a kind capable of determining any other character of the structure, such as its weight, moment of inertia, resonance condition. The data processing and analyzing utility of the verification assembly may be preprogrammed such as to allow the presentation of said predetermined output sensory perceptible by a human being, only if data generated by the measuring unit matches at least a part (fragment) of the specific structure signature (forming a part of the structure-related data previously recorded on a readable medium). The readable medium may and may not be incorporated in the presentation case. In other words, the measured character of the structure presents a key code to the predetermined output representative of the structure-related data.

It should also be noted that, in the case of gemstones, the presentation case according to the invention may also include a rough model of the gemstone.

A structure to be sold may be of a kind provided with an identification code (incorporated in or attached to the structure), the code being indicative of a structure- and/or structure-manufacturer- and/or structure-vendor-related data. For example, a structure may carry the structure-manufacturer trademark incorporated in the structure, e.g., by means of a hologram readable by IR radiation. A method of selling such a structure enables various options of the structure presentation to a structure-receiver.

Thus, according to yet another aspect of the present invention, there is provided a method of selling a structure characterized by a specific structure signature in the form of a specific radiation response to predetermined incident radiation, the method comprising the steps of:

providing data representative of said specific structure signature to be included in the entire structure-related data;

providing a database containing various types of information, and allowing selection of at least one of said types of information to be included in the entire structure-related data; and creating a predetermined output representative of the entire structure-related data, wherein said output includes a non-visual portion derived from the specific structure signature and being sensory perceptible by a human being.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 1 shows a schematic layout of the various equipment for producing of the song of a gemstone; FIG. 2 is a perspective view of a jewellery box for holding of a gemstone and playing of the song of the gemstone; and FIG. 3 is a schematic layout of the circuitry of the jewellery of FIG. 2;

DETAILED DESCRIPTION OF THE INVENTION

More specifically the present invention is used for representing such structures as gemstones, typically diamonds, e.g., as part of a jewelry piece, and is therefore described below with respect to this application. It should, however, be noted that for the purposes of the present invention such a structure or body (animated or not) may be of any kind, not necessarily transparent or translucent, provided it is characterized by a specific radiation response (structure signature) in the form of a pattern coming from the structure in response to a predetermined incident radiation. Such a structure that is characterized by a specific radiation response may, for example, be a picture or a sculpture.

Figure 1:
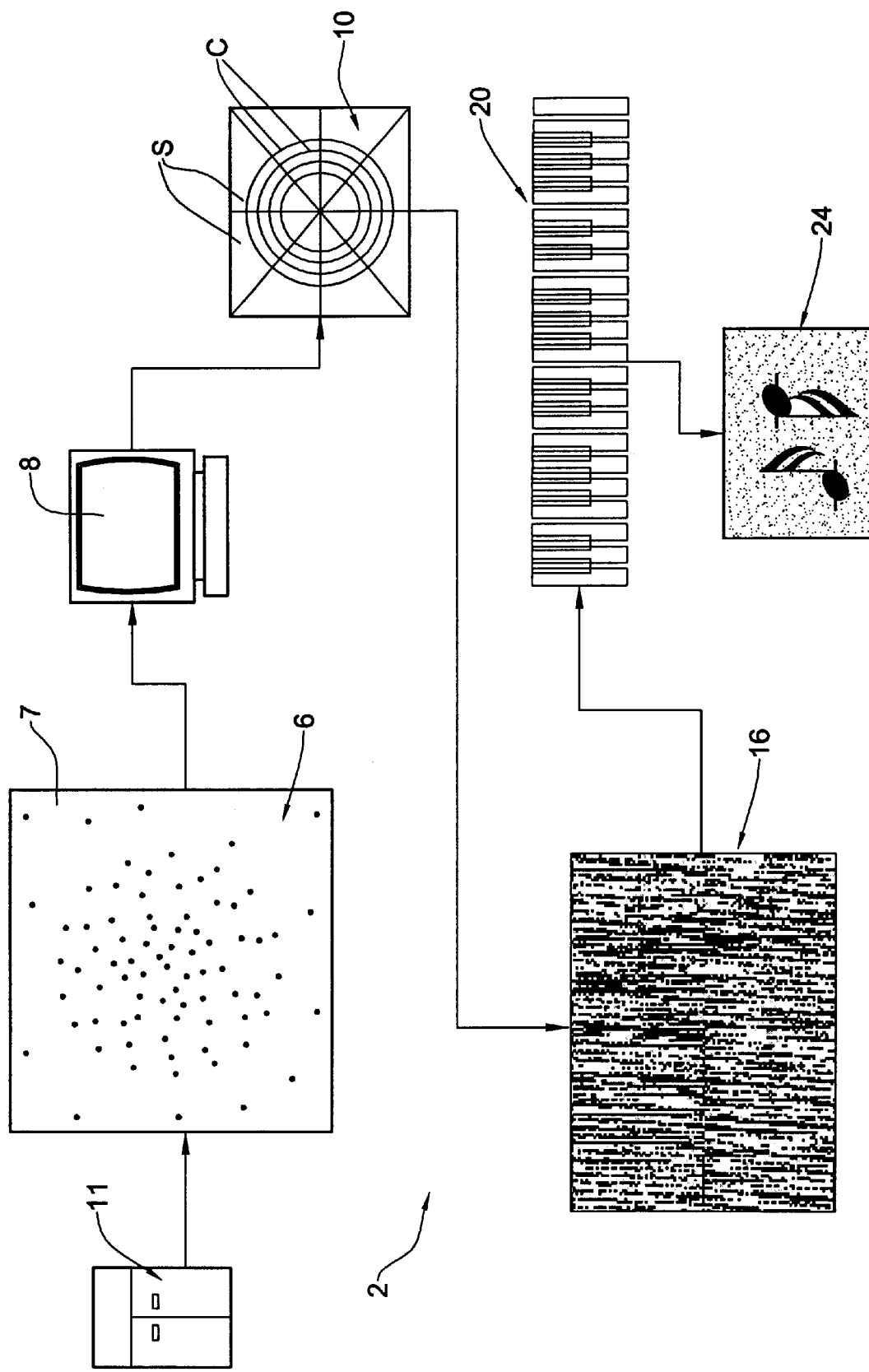
FIGS. 1 to 3 illustrate one possible example of the invention, wherein such a structure as a gemstone is represented by such as output as a song.

Referring to FIG. 1, there is illustrated a system, generally designated 2, constructed and operated according to the invention for producing a musical output (constituting a predetermined non-visual output sensory perceptible by a human being) based on the optical signature of a gemstone (constituting a specific structure signature). In the present example, the system comprises a scanner 4 (generally, an optical system composed of a light source and a detector) for scanning the gemstone (which is not specifically shown) and producing an optical response of the gemstone defined by its reflection and refraction characteristics. For this purposes, the relative movement between the gemstone and a light source of the scanner 4 is provided (typically by rotating the gemstone about its axis).

It should, however, be noted that, for the purposes of the present invention, the scanner 4 can be replaced by another optical response recording arrangement, for example such where no scanning of a gemstone is required, and its optical response is collected (e.g., by an area CCD camera) by directing incident radiation onto the gemstone along its central axis (due to multiple directions of propagation of reflected and refracted light components inside the diamond).

Turning back to FIG. 1, an electrical output of the scanner representative of the optical response of the gemstone is processed by a suitable processing utility (not shown) and a bitmap 6 (the so-called "gemprint") corresponding to the optical response is produced. As shown, the bitmap 6 is indicative of a number of hot spots 7 in the gemstone corresponding to reflected light beams.

If the gemstone is correctly supported in the scanner 4, these hot spots (points) can be produced. Full 360°-rotation is permitted to compare two gemprints. If there is misalignment of the axis of the gemstone, there will be a distortion of the position of the hot spots. If the gemstone is correctly positioned by a skilled technician, there is only a small degree of variation in the gemprint. It is also possible to support the gemstone in an adjustable manner to allow correction of the alignment of the axis in a mechanized manner.

The system 2 further comprises a data processing station 8 (which, together with the above-indicated processing utility, constitutes a data processing and analyzing utility), where the digitized bitmap 6 is further processed to produce a predetermined output representative of the entire gemstone-related data. According to the present example, the bitmap 6 is analyzed to produce a final pattern 10, i.e., the so-called "summarized information" of the bitmap 6. To this end, the bitmap 6 is divided into a number of concentric circles, generally at C, and a number of segments, generally at S. Each of the concentric circles defines a region which can be summarized for the hot spots. In this way, the rotational position of the diamond is not critical as the bitmap will be summarized using the concentric circles. It is also possible to look at the information within limited portions of the concentric circles, using small segments, and comparing the values of different segments to determine whether a gemstone is the same. There can be logic associated with this for determining where the initial data representing the start of the song occurs, such that each song can be consistent. In many cases, the summary using concentric circles itself, is sufficient to distinguish one gemstone from another and to create the unique of the diamond.

Based on the summarized information of the bitmap (final pattern FP), a sound file 16 is produced (by a suitable data translator utility, which is not specifically shown here). There are various known algorithms for translating a bitmap sequence to a sound file. This sound file is then used to produce the song of the diamond. The melody file can include the composition of a variation of the musical theme. Such variations of the theme is identifiable and recognizable by a variation of one or more of its parameters, such as pitch, interval between notes, key, contour, rhythm and tempo. The song file preferably will be enhanced using an arrangement 20 (which may be part of the translator utility) to create a song which is pleasing to the ear. For example, certain notes or scales can be enhanced using harmonics to improve the actual song played by an output device 24. A simplified song can use bell tones. Such techniques are known in the art and therefore need not be specifically described.

Thus, that the sound file 16, which is based on the optical response of the gemstone, is used to produce a song of the diamond. Depending upon the length of a song and the amount of information that is summarized, the song of the gemstone can uniquely identify a particular gemstone. In some applications, it may be sufficient that the song is based on the inherent characteristics of the stone, and it is not necessary, for the song alone, to uniquely identify the stone or other translucent material.

The processing of the optical signature of a gemstone, crystal or other translucent, natural or synthetic stone, as described in FIG. 1, produces the song of the gemstone which is recorded for sale with the store. As shown in FIG. 1, according to one possible algorithm of a technique for translating the optical signature to a song, the optical signature (bitmap) is divided into sectors and concentric circles to define regions, and the number of hot spots in each region is counted. Other coding methods can be used.

As can be appreciated, the song can be relatively simple based on such instruments as bells or could be based on a string orchestra, or a combination of different instruments. The important aspect is that the optical response of the gemstone can be used to produce a specific sound file or a sound file which accurately reflects the characteristics of the gemstone.

It should be understood that since the optical signature is specific to a gemstone or other translucent structure, the resulting sound is specific to this structure of this kind of structures. As the sound is created from a binary file generated by the relative size and/or position of each "hot spot", special attention should be paid to the harmony of the music created. The conversion (translation) algorithm will process the sound created and insert additional notes to bridge, if necessary, less compatible notes in accordance with established conventions. Such a conversion may allow for producing variations of the basic musical theme, by changing one or more of the musical parameters, thus producing a pseudo "Bach", "Mozart", etc. compositions. For example, the algorithm can allow for modulating the tempo to produce more contemporary music, such as jazz and blues type compositions, while choosing the appropriate sound generators. Such a musical variation can also be done by a musician, and its result converted to a file stored in the system. A minimum and maximum length of the melody will be specified. The algorithm modifies the data in a predetermined manner and is therefore repeatable. The algorithm can also introduce notes or pairs of notes which are readily distinguishable from the music, which directly corresponds with the optical signature. Thus, the algorithm preferably translates the optical signature to music and also enhances the music in a predetermined manner.

Figure 2:
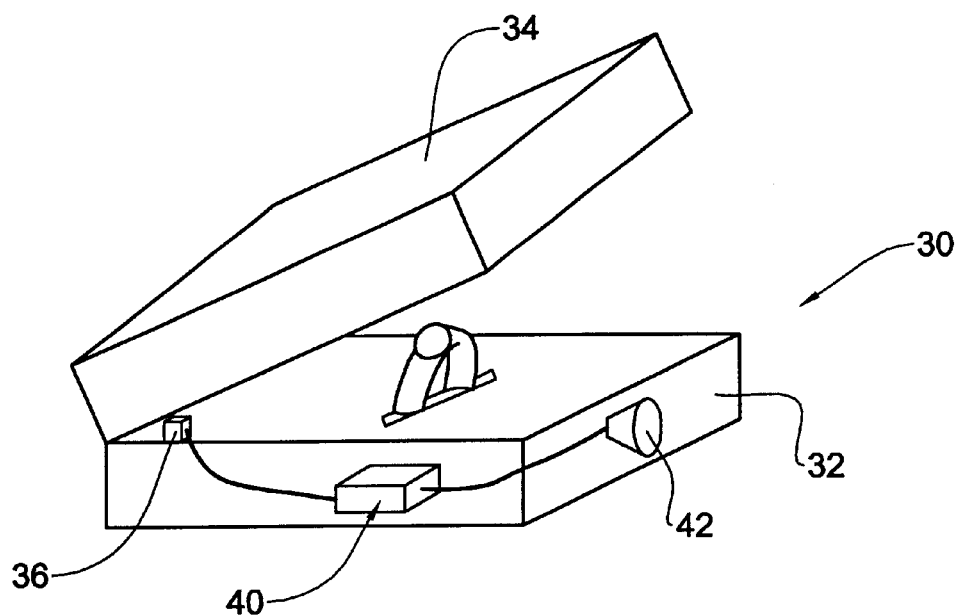

Reference is made to FIG. 2 showing a jewellery box 13, which will be used for storing of the gemstone. The box 13 includes a base 32 and a hinge top 34. An actuator 36 determines when the lid of the box has been moved to an open position. This actuator then initiates a processing arrangement 40, preferably a sound chip, to produce an output signal which is fed to a speaker 42 for playing the song of the gemstone which has been recorded with the processing arrangement 40.

Figure 3:
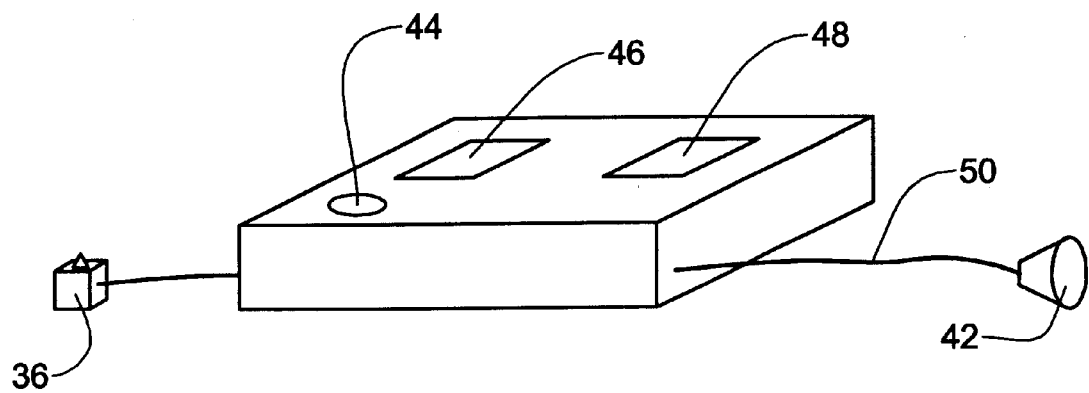

FIG. 3 shows the actuator 36 which provides a start signal to the processing arrangement 40, having a replaceable or rechargeable battery 44, a memory 46 for storage of the song of the gemstone, and a processor 48. The processor 48 produces an output signal 50 which is fed to the speaker 42, and the song of the diamond is played.

The musical song of the diamond can be played over a base song, and, if desired, can be placed using different instruments. The musical representation of the stone, preferably, is unique, and as such, is a musical equivalent of the optical signature. In some cases, the musical conversion (translation) needs no provision of a unique musical equivalent. It may be sufficient to produce a musical representation of the characteristics of the stone.

Generally speaking, a system for representing a structure (e.g., diamond) according to the invention comprises such main constructional parts as an optical assembly, a data processing and analyzing utility, and a data presentation utility. The optical assembly is composed of a radiation source and a radiation detector. Turning back to FIG. 1, the following should be noted.

In this specific example, the system 2 is an electro-optical system, namely utilizes optical means for producing and detecting light response of the diamond. More specifically, the radiation source is a light source, for example a laser generating a collimated light, and the detector is of a kind sensitive to light signals to generate electrical output representative thereof, for example a photodiode. The detector may be accommodated in a manner to receive either light returned (reflected/refracted) from the diamond, or light transmitted therethrough. The light source may be composed of light emitting elements generating light components of different wavelengths, or light emitting elements arranged so as to illuminate the structure at different angles of incidence.

The data processing and analyzing utility (i.e., suitable hardware operable by suitable software) is operable for processing the signal generated by the detector and producing a digitized bitmap indicative of the detected light response of the diamond to be included in the entire diamond-related data generated by the processing and analyzing utility. Optionally, the processing and analyzing utility is preprogrammed for further processing the bitmap 6 to produce a final pattern 10. The processing and analyzing utility comprises a suitable translation means for translating the bitmap BM (or final pattern 10, as the case may be) to produce an output signal in a predetermined format sensory perceptible by a human being (as will be described more specifically further below).

Figure 4:
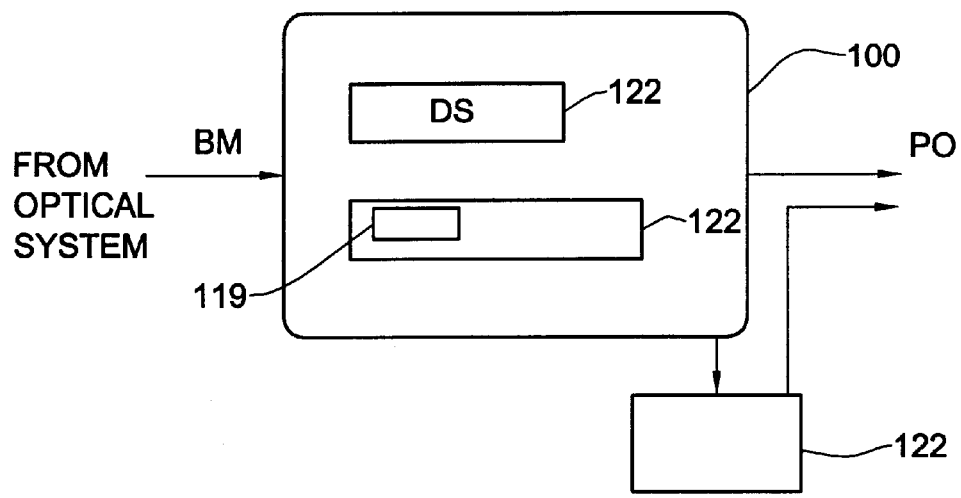
FIG. 4 is a schematic illustration of a system according to the invention for representing a structure-related data suitable to be used in combination with any signature recording arrangement.

Referring to FIG. 4, there are illustrated by way of a block diagram, main components of a system 100 according to the invention for representing a structure, e.g., a diamond, suitable to be used in combination with any structure signature recording arrangement, e.g., that commercially available from Gemprint Corporation. The system 100 comprises a data processing and analyzing utility 110, and a memory 120. The utility 110 is operable for processing input data in the form of a bitmap BM representative of the radiation response of a diamond as obtained in the signature recording arrangement, and producing a predetermined output PO. The latter is representative of the entire diamond-related data and is sensory perceptible by a human being. To this end, the data processing and analyzing utility comprises a suitable translator utility 119. The memory 120 serves for storing one or more databases DB containing information to be included in the output representative of the entire diamond-related data. Optionally, the system 100 is also associated with a chemical assembly 122 for including a specific perfume into the predetermined output, as the case may be. The output is of a kind to be received by a suitable data presentation utility (speaker, display) 124 for presenting the output.

The final pattern makes it possible to analyze the information within the limited portions of the concentric circles, using small segments, and comparing the values of different segments. In many cases, the summary using concentric circles itself is sufficient to distinguish one diamond from another and to create the unique signature of the diamond. Practically, data indicative of the part of the signature, for example relating to one or several segments (i.e., a fragment of the entire signature), may be used as a key code to the entire signature. This enables authentication of the structure, i.e., enables to determine whether a structure under inspection is that representative by a specific previously recorded bitmap.

The translator utility 119 is of appropriate type to format the bitmap or its summarized information (i.e., final pattern) into a desired output. This may be an audio signal (e.g., music, message), and/or visual signal (e.g., simple light pattern, image and/or message to be displayed). Additionally, the chemical assembly 122 and a respective database part may be utilized to include a perfume-related data in the output. A translation technique may be of any known suitable type, and does not form a part of the present invention.

If a diamond identification code is presented in the diamond girdle, it can be read by the same electro-optical system (that may and may not utilize an additional detector) and may be included in the diamond signature. It should be noted, although not specifically shown, that the system according to the invention may also be equipped with a measuring unit of a kind capable of determining one or more characters of the diamond and generating data indicative thereof. Such characters may include the diamond's weight and/or its moment of inertia.

The output, while being desirably formatted and being indicative of the diamond specific signature, may also contain data indicative of a diamond manufacturer- and/or diamond vendor-related information. For example, a diamond as received from its manufacturer and intended for sale, may be supplied together with a readable medium (information carrier), such a disc or flash-memory card on which the diamond signature related data and the manufacturer-related data are recorded, presenting together at least a part of the entire diamond-related data.

Alternatively or additionally, the output comprising data representative of the diamond signature, may also be indicative of data related to the diamond purchaser/receiver selected from the databases stored in the memory 120 in accordance with the purchaser/receiver preferences (e.g., astrological data).

Figure 5:
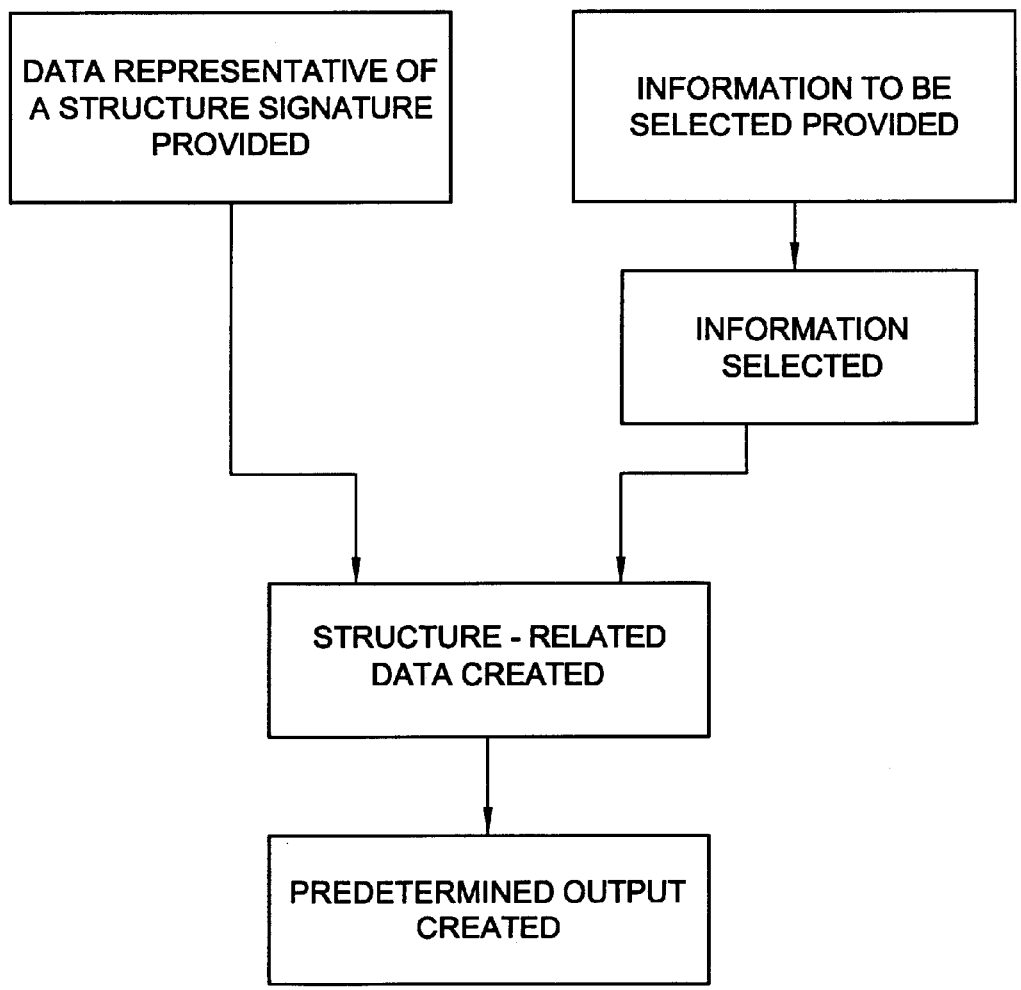
FIG. 5 is a flow chart of the main steps in a method of selling a structure (e.g., diamond) according to the invention.

Referring to FIG. 5, there is illustrated a flow chart of the main steps in a method of selling a diamond according to the invention. In the present example, each diamond intended for sale is associated with its specific information carrier containing either the entire data representative of the diamond signature (and, optionally also representative of the diamond-manufacturer) or a part (fragment) thereof, which is also specific for the diamond. The diamond may be supplied in a presentation case with the information carrier installed therein. A purchaser, while selecting a specific diamond, is invited to select (from the databases) the specific output sensory perceptible to a human being, e.g., song, melody, audio and/or visual message, a series of various messages and, optionally, a manner in which they are to appear to the diamond receiver, perfume, etc. In other words, the purchaser can choose the output indicative of the purchaser/receiver-related information. Thus, the data representative of the diamond as supplied for selling purposes, together with the purchaser/receiver-related data, present the entire diamond-related data, that can be presented in a manner sensory perceptible by a human being, as selected by the diamond purchaser. This output, while being created by the processor unit, is stored in a data representing utility in manner to be reproducible by a suitable data retrieval utility. The purchaser may choose that the selected output is to be transmitted to his (or to the other diamond receiver's) personal communication unit from the diamond's seller side (through a communication network) so as to be retrieved whenever the receiver desires. Alternatively or additionally, the data representing utility is supplied to the diamond purchaser together with the diamond presentation case, while the data retrieval utility may and may not form a part of the diamond presentation case.

Figure 6A:
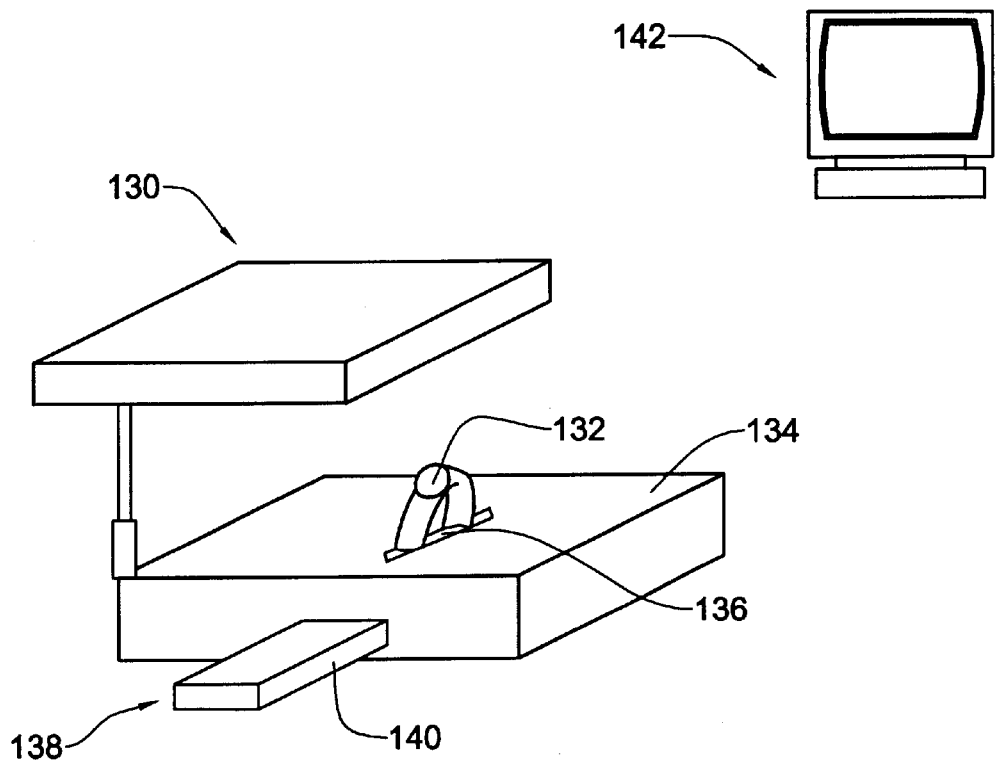
FIGS. 6A to 6C schematically illustrate three different examples, respectively, of a structure presentation device according to the invention.
Figure 6B:
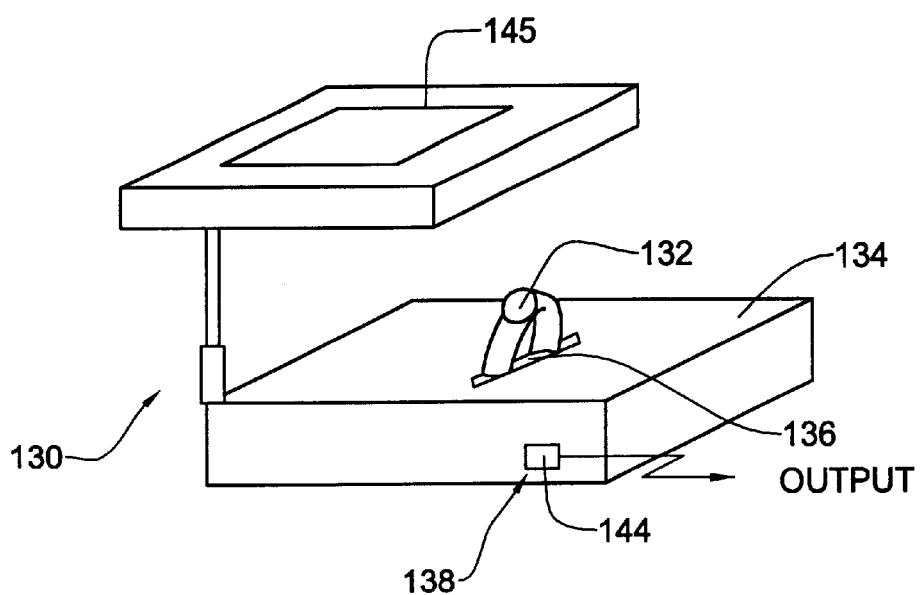
Figure 6C:
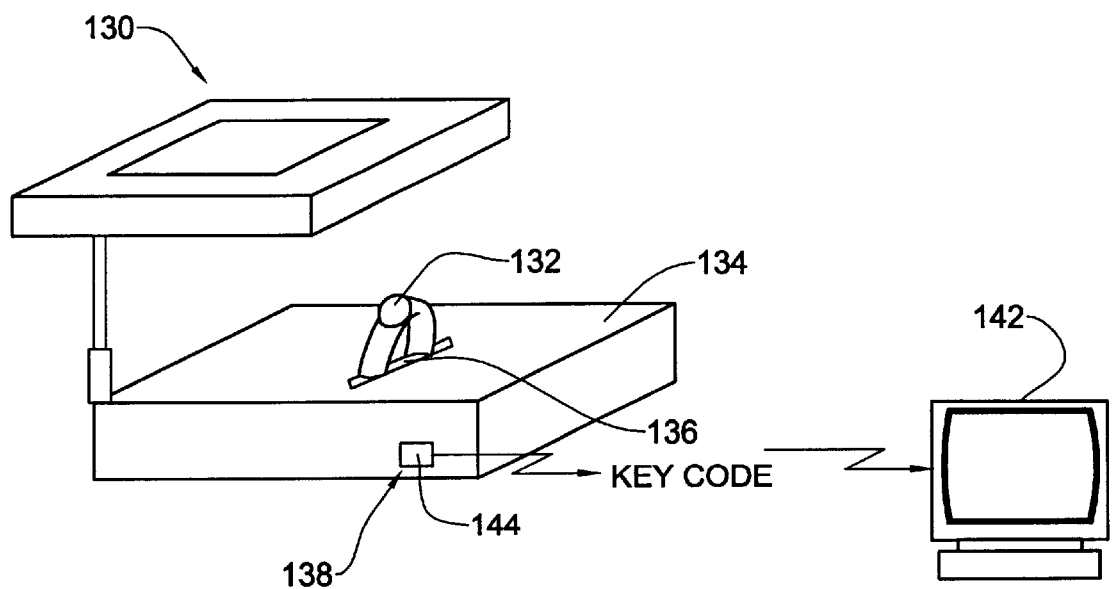

Reference is made to FIGS. 6A–6C illustrating three different examples of a device 130 for presentation of a purchased structure 132 (diamond in the present example which is shown as a part of a jewelry piece). To facilitate understanding, the same reference numbers are used for identifying components, which are identical in these three examples.

The device 130 is composed of a box 134 (constituting a presentation case) having a support member 136 for supporting the diamond 132, and is equipped with a data representing utility 138 enabling the presentation of the diamond-related data by means of a predetermined output. This predetermined output is previously created while purchasing the diamond. To this end, the purchaser selects from the databases (DB in FIG. 4) information to be included in the output. For example, the output may include a message "HAPPY BIRTHDAY" and an image of a corresponding gemprint bitmap hot-spots, possibly, together with the person's astrological map to be displayed.

In the example of FIG. 6A, the utility 138 enabling the presentation of the output is in the form of a readable medium 140 (disc) to be read by an external data retrieval unit 142 (e.g., a computer or the like device), which is typically available at every home or office. What can actually be recorded on the readable medium may and may not include the output representative of the entire-diamond-related data. For example, only the data representative of the diamond in the case (its signature and, optionally, manufacturer- and/or vendor-related data) may be stored on the medium 140. The stored data, when being identified by the computer, presents access to the predetermined output, as selected by the diamond purchaser and stored at a specific WebSite relating to the diamond retailer to be accessed through the Internet. In other words, when the purchaser selects his related output to be presented to a receiver (for whom he purchases the diamond), this output is stored at the retailer site, which includes suitable software capable of performing the following: in response to a file recorded on the readable medium and transmitted from the external unit to the retailer site through the communication network, actuates the transmission of the output to the external unit.

It should, however, be noted that for the purposes of selling a structure characterized by a specific structure signature, the structure can be sold simply with a data representing utility 138 comprising only a readable medium 140 (disc) to be read by an external data retrieval unit 142. In this specific example of a gemstone-like structure, it is typically the case that the structure is supplied in a case.

In the example of FIG. 6B, the utility 138 enabling the representation of the output signal comprises an electronic assembly 144 mounted in the box 134 (e.g., including a chip with embedded application). The assembly 144, while being actuated by an actuator (which is not specifically shown, and which may be a press button or an automatic actuator responsive to the opening of the box), starts the presentation of the previously created output (e.g., song, melody, and/or message). In other words, the electronic assembly incorporates both a memory storing the previously created output, and a data retrieval utility reproducing this output. In the present example, the electronic assembly 144 also includes an LC display 145 mounted on the box so as to be exposed to the receiver. A model of the rough of the respective diamond, prior to being cut and polished, may be displayed to the diamond receiver.

In the example of FIG. 6C, the utility 138 comprises the electronic assembly 144 to be used in combination with an external data retrieval unit 142 (e.g., computer). The assembly 144 is connectable to the external unit 142 either through wires or wireless (RF or infrared signal), and an output signal generated by the electronic assembly is indicative of a key code transmittable to the external unit 142. For example, a purchaser/receiver may select the output representative of the diamond-related data in the form of a specific message and/or image, which can be retrieved from a computer file in response to the key code supplied from the device 130. This key code may be representative of a specific fragment (e.g., data based on some of the segments in the final pattern FP) of the specific diamond signature. The signal representative of this fragment thus presents access to the entire diamond-related data available on the external unit 142, e.g., through the Internet. This actually enables the authentication of the diamond in the box.

It should be noted, although not specifically shown, that in any one of the above examples, a chemical assembly (122 in FIG. 4) may also be included in the device 130, provided the diamond purchaser/receiver has selected the perfume (from a corresponding database) to form the part of the output signal.

Figure 7:
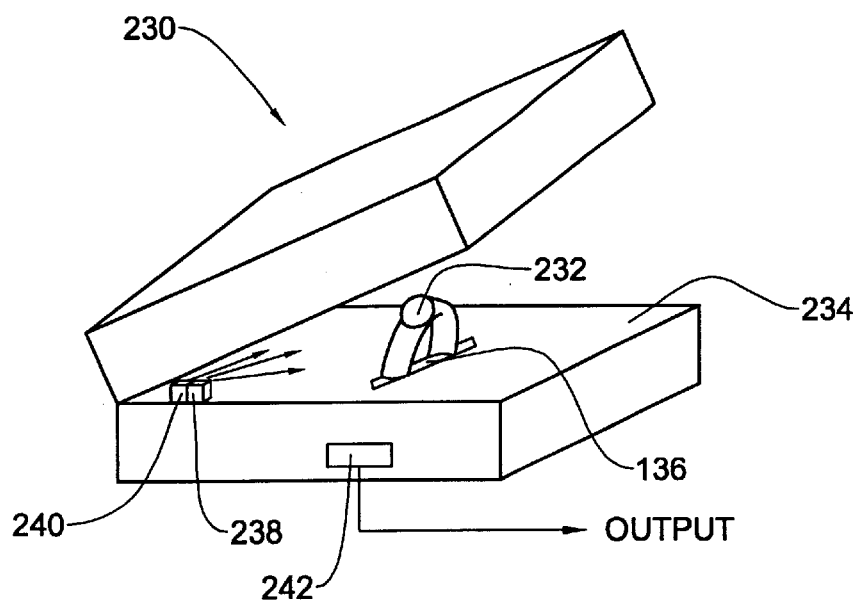
FIG. 7 is one more example of a device for representing data indicative of a purchased structure according to the invention.

Turning now to FIG. 7, there is illustrated another possible example of a device 230 for representing data indicative of a purchased diamond 232. In device 230, the data representing utility comprises a verification system 234 installed in a box 236 containing the diamond 232. The system 234 comprises a measuring unit, which, in the present example, includes an optical system composed of a light source 238 for illuminating the diamond to produce a light response of the diamond, a detector 240 for detecting the light response, and a processor unit 242 for generating the output signal. Generally, such an optical system may include the entire Gemprint system. Alternatively, the optical system may be designed such that its light source (lamp or laser) illuminates the diamond such that a light response of only a part of the diamond can be detected, and therefore the processing technique has to deal only with the fragment of the entire diamond signature. For example, this can be implemented by rotating the jewelry piece with the inserted diamond (by appropriately rotating the support member 136) and thereby scanning a part of the diamond. The processor is equipped with a memory chip (not shown) that stores the output representative of the entire diamond-related data (the entire diamond signature and additional information (e.g., message) as selected by the diamond purchaser/receiver). Thus, if the detected fragment matches the diamond signature as included in the previously created and stored output, the processor generates this output to be presented to the diamond receiver. The measuring unit of the verification system may include, as an alternative to an optical system or in addition thereto, a suitable means for measuring the diamond's weight (e.g., a piezoelectric element), or the diamond's moment of inertia, in which case the diamond is mounted for rotation inside the box. It should be noted that such a verification system may be of a kind utilizing an identification code assigned to a jewelry piece in the case and incorporated in the jewelry piece of attached thereto, other than the optical signature of the gemstone. This may, for example, be implemented as identification of the code by optical means, or of the so-called "attachable electronic chips".

Those skilled in the art will readily appreciate that various modifications and changes can be applied to the preferred embodiments of the invention as hereinbefore described without departing from its scope defined in and by the appended claims. For example, any kind of structure (body) characterized by a specific structure signature in the form to a specific radiation response can be represented by the technique of the present invention, as well as any kind of information can be included in the output sensory perceptible by a human being, provided this output comprises a non-visual portion derived from the the specific structure signature.

What is claimed is:

1. A method for representing a transparent or translucent structure of a kind characterized by a specific radiation response to a predetermined incident radiation, the method comprising the steps of:
   (a) applying the incident radiation to the structure to produce the specific radiation response thereof;
   (b) detecting said specific radiation response and generating data indicative thereof;
   (c) processing the generated data using a musical translation algorithm to produce an audio signal having a musical segment based on the generated data; and
   (d) using said audio signal to produce an output corresponding to the structure wherein said output includes said musical segment produced by said audio signal.

2. The method according to claim 1, wherein the incident radiation is optical.

3. The method according to claim 1, wherein said output is formatted for presentation through a communication network.

4. The method according to claim 1, wherein said output includes data related to at least one of the following: structure-manufacturer, structure-vendor and structure-receiver.

5. The method according to claim 1, wherein the output additionally includes a visual signal.

6. The method according to claim 5, wherein the visual signal is of a kind to be displayed on a monitor.

7. The method according to any one of claims 1 and 5, wherein the output includes a perfume.

8. The method according to claim 1, wherein said structure comprises a gemstone.

9. The method according to claim 8, wherein said specific radiation response is unique for a specific gemstone.

10. The method according to claim 1, wherein said structure is of a kind being reproducible by a manufacturing process, said specific radiation response being specific for the reproducible structures.

11. The method according to claim 10, wherein said structure is selected from the group consisting of a gemstone, a diamond and a crystal object.

12. The method according to claim 9, wherein the structure is a diamond and the output includes the data corresponding to the optical signature of the diamond and of data presented on the diamond girdle or table.

13. A system for representing a transparent or translucent structure of a kind characterized by a specific radiation response to a predetermined incident radiation, the system comprising:
   (One) a radiation source generating the incident radiation to be applied to said structure to produce the specific radiation response thereof;
   (Two) a detector means for detecting the specific radiation response and generating data indicative thereof;
   (Three) a data processing and analyzing utility for processing the generated data using a musical translation algorithm to produce a corresponding audio signal having a musical segment derived from said data and using said audio signal to produce an output having said musical segment; and
   (Four) a data presentation utility for presenting said output.

14. The system according to claim 13, and also comprising a database representative of various kinds of additional information to be selected by an authorized person and included in the output.

15. The system according to claim 14, wherein said additional information to be included in the output comprises data related to at least one of the following: structure-manufacturer, structure-vendor and structure-receiver.

16. A system for representing a transparent or translucent structure of a kind characterized by a specific radiation response to a predetermined incident radiation, the system comprising:
   a data processing and analyzing utility having a translation algorithm for processing a bitmap corresponding to said specific radiation signature and producing an output representative of a structure-related data, wherein said output includes a musical portion translated from at least a portion of said specific radiation response; and
   a data presentation utility for presenting said output including playing said musical portion.

17. A device for presentation of a transparent or translucent structure, which is characterized by a specific structure signature in the form of a specific radiation response of the structure to predetermined incident radiation, the device comprising a data representing utility operable to generate a signal, which enables presentation of a predetermined output representative of structure-related data, wherein said predetermined output includes a musical segment produced using a translation algorithm which uses the specific radiation response as an input signal for the translation algorithm.

18. A device for presentation of a transparent or translucent structure, which is characterized by a specific structure signature in the form of a specific radiation response of the structure to predetermined incident radiation, the device comprising: a presentation case for containing the structure therein; and a data representing utility operable to generate a signal, which enables presentation of a predetermined output representative of structure-related data, wherein said predetermined output includes a musical portion translated from said specific structure signature using a musical translation algorithm.

19. The device according to claim 18, wherein the data representing utility comprises a readable media for storing the structure-related data, the generated signal being of a kind readable by an external data retrieval unit having a data presentation utility capable of generating said predetermined output.

20. The device according to claim 18, wherein the data representing utility comprises a readable media storing a specific fragment of the data representative of the structure signature, the fragment presenting access to the entire structure-related data available on an external data retrieval unit having a data presentation utility capable of generating said predetermined output.

21. The device according to claim 18, wherein the data representing utility comprises a readable media storing the structure-related data and a data retrieval unit having a data presentation utility capable of generating said predetermined output.

22. The device according to claim 21, wherein said data presentation utility comprises a speaker.

23. The device according to claim 21, wherein said data presentation utility comprises a display.

24. The device according to claim 18, and also comprising a structure signature verification assembly installed in the presentation case and associated with said data representing utility, the verification assembly comprising a measuring unit of a kind capable of determining a character of the structure and generating data indicative thereof, and a data processing and analyzing utility, the data representing utility thereby enabling presentation of the predetermined output, if the data indicative of the determined character of the structure matches a corresponding data part of the structure signature.

25. The device according to claim 24, wherein said measuring unit comprises a radiation source and a detector.

26. A presentation case for containing a transparent or translucent structure to be purchased, wherein the structure is characterized by a specific structure signature in the form of a specific radiation response of the structure to predetermined incident radiation, the presentation case comprising a verification assembly, which comprises:

a measuring unit of a kind capable of determining a character of the transparent or translucent structure presenting at least a part of the structure signature, and capable of generating data indicative of said character, and a data processing and analyzing utility of a kind having a musical translation algorithm capable of generating an output signal that includes a translated musical segment that enables a musical presentation of the structure signature, if the data generated by the measuring unit matches a previously stored data representative of the structure signature.

27. The presentation case according to claim 26, and also comprising a data presentation utility for presenting a predetermined output that includes said musical portion at least partially corresponding to said specific structure.

28. A method of selling a transparent or translucent structure characterized by a specific structure signature in the form of a specific radiation response of the structure to predetermined incident radiation, the method comprising the step of providing a data representing utility having a translation algorithm operable to generate an audio signal, which enables presentation of a predetermined output representative of structure-related data, wherein said predetermined output includes a musical segment translated from said specific structure signature, said data representing utility being supplied with the structure to be sold.

29. A method of selling a transparent or translucent structure characterized by a specific structure signature in the form of a specific radiation response of the structure to predetermined incident radiation, the method comprising the steps of: providing data representative of said specific structure signature of said transparent or translucent structure to be included in the entire structure-related data; providing a database containing various types of information, and allowing selection of at least one of said types of information to be included in the entire structure-related data; and allowing creation of a predetermined output representative of the entire structure-related data, wherein said output includes a musical segment translated from the specific radiation response of the structure.

30. The method according to claim 29, and also comprising the step of: providing a data representing utility operable to generate a signal to cause presentation of said predetermined output in said musical segment, said data representing utility being for selling with the structure.

31. The method according to claim 30, and also comprising the step of: equipping a presentation case for containing said structure with a verification assembly for determining a character of the structure and generating data indicative thereof, such that said predetermined output can be presented, if the generated data indicative of the determined character of the structure matches a corresponding data part of the structure signature.

32. The method according to claim 30, wherein the data representing utility comprises a readable media storing the structure-related data, the output signal being of a kind readable by an external data retrieval unit having a data presentation utility capable of generating said predetermined output.

33. The method according to claim 30, wherein the data representing utility comprises a readable media storing a specific fragment of the data representative of the structure signature, the fragment presenting access to the entire structure-related data available on an external data retrieval unit having a data presentation utility capable of generating said predetermined output.

34. The method according to claim 30, wherein the data representing utility comprises a readable media storing the structure-related data and a data retrieval unit having a data presentation utility capable of generating said predetermined output.

* * * * *